(12) United States Patent
Ranganathan et al.

(10) Patent No.: US 12,106,496 B2
(45) Date of Patent: Oct. 1, 2024

(54) LOWER TO HIGHER RESOLUTION IMAGE FUSION

(71) Applicant: KONINKLIJKE PHILIPS N.V., Eindhoven (NL)

(72) Inventors: Vaitheeswaran Ranganathan, Bangalore (IN); Saravanan Karunanithi, Chennai (IN); Rohinee Nuggehalli Ashwinee Kumar, Bangalore (IN); Bojarajan Perumal, Bangalore (IN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 681 days.

(21) Appl. No.: 17/052,200

(22) PCT Filed: May 1, 2019

(86) PCT No.: PCT/EP2019/061154
§ 371 (c)(1),
(2) Date: Nov. 1, 2020

(87) PCT Pub. No.: WO2019/211334
PCT Pub. Date: Nov. 7, 2019

(65) Prior Publication Data
US 2021/0056717 A1 Feb. 25, 2021

(30) Foreign Application Priority Data
May 1, 2018 (EP) .................................. 18170235

(51) Int. Cl.
*G06K 9/00* (2022.01)
*A61B 5/00* (2006.01)
(Continued)

(52) U.S. Cl.
CPC ............ *G06T 7/337* (2017.01); *A61B 5/0035* (2013.01); *A61B 5/004* (2013.01); *A61B 5/7267* (2013.01);
(Continued)

(58) Field of Classification Search
CPC .................. G06T 7/337; G06T 7/0012; G06T 2207/10081; G06T 2207/10088;
(Continued)

(56) References Cited

U.S. PATENT DOCUMENTS 7,715,899 B2 5/2010 Harvey
2010/0067768 A1* 3/2010 Ionasec .................. G06T 7/344
382/128

(Continued)

FOREIGN PATENT DOCUMENTS

CN 107730567 A 2/2018
EP 3246875 A2 11/2017
WO WO2009053896 A2 4/2009

OTHER PUBLICATIONS

PCT International Search Report, International application No. PCT/EP2019/061154, May 29, 2019.
(Continued)

*Primary Examiner* — Hadi Akhavannik
(74) *Attorney, Agent, or Firm* — Sherry Austin

(57) ABSTRACT

Described are various embodiments of systems, devices, methods, and computer readable mediums related to image fusion of lower resolution (LR) images and higher resolution (HR) reference images of an object in a body. In an example embodiment of a method, the method comprises determining specific image scanning geometries used for acquiring LR images based on an ML algorithm that uses at least one feature in at least one region of interest in the respective LR images as input. The method further comprises generating
(Continued)

image scanning geometry matching oblique HR images based on HR reference images and the determined specific image scanning geometries used for acquiring the respective LR images and registering the oblique HR images with the LR images to generate registered HR images. Current feature information is extracted from the LR images and mapped on corresponding feature information in the registered HR images to generate fusion images.

18 Claims, 8 Drawing Sheets

(51) Int. Cl.
*A61B 6/00* (2006.01)
*G06T 7/00* (2017.01)
*G06T 7/33* (2017.01)
*G16H 30/20* (2018.01)
*G16H 30/40* (2018.01)
*G16H 50/20* (2018.01)
*A61B 5/055* (2006.01)
*A61B 6/03* (2006.01)

(52) U.S. Cl.
CPC .......... *A61B 6/5247* (2013.01); *G06T 7/0012* (2013.01); *G16H 30/20* (2018.01); *G16H 30/40* (2018.01); *G16H 50/20* (2018.01); *A61B 5/055* (2013.01); *A61B 6/037* (2013.01); *G06T 2207/10081* (2013.01); *G06T 2207/10088* (2013.01); *G06T 2207/10132* (2013.01); *G06T 2207/20081* (2013.01); *G06T 2207/20221* (2013.01); *G06T 2207/30096* (2013.01)

(58) Field of Classification Search
CPC . G06T 2207/10132; G06T 2207/20081; G06T 2207/20221; G06T 2207/30096; G06T 2207/20084; G06T 2207/10112; G06T 2207/20076; G06T 2207/20104; G06T 2207/30068; G06T 2207/30244; G06T 7/11; G06T 7/33; G06T 7/73; G16H 30/20; G16H 30/40; G16H 50/20; A61B 5/0035; A61B 5/004; A61B 5/7267; A61B 5/055; A61B 6/5247; A61B 6/037
See application file for complete search history.

(56) References Cited

U.S. PATENT DOCUMENTS

2013/0039555 A1* 2/2013 Xu .............................. G06T 7/38
 600/443
2017/0132796 A1 5/2017 Popovic
2017/0337682 A1* 11/2017 Liao .......................... G06T 7/30
2020/0397334 A1* 12/2020 Fang ....................... G06N 3/045

OTHER PUBLICATIONS

Ghesu F.C. et al., "Marginal Space Deep Learning: Efficient Architecture for Volumetric Image Parsing", IEEE Transactions on Medical Imaging, IEEE Service Center, Piscataway, NJ, US, vol. 35, No. 5, May 1, 2016 (May 1, 2016), pp. 1217-1228, XP011607957.
Ferrante E. et al., "Slice-to-Volume Medical Image Registration: A Survey", Medical Image Analysis, Oxford University Press, Oxofrd, GB, Apr. 28, 2017 (Apr. 28, 2017), XP085107048.
Kaya M. at al., "Needle Localization Using Gabor Filtering in 2D Ultrasound Images", 2014 IEEE International Conference on Robotics and Automation (ICRA), IEEE, May 31, 2014 (May 31, 2014), pp. 4881-4886, XP032650211.
Yan P. et al., "Discrete Deformable Model Guided by Partial Active Shape Model for TRUS Image Segmentation", IEEE Transactions on Biomedical Engineering, IEEE Service Center, Piscataway, NJ, USA, vol. 57, No. 5, May 1, 2010 (May 1, 2010), pp. 1158-1166, XP011343227.
Pardasani U. et al., "Single Slice US-MRI Registration for Neuro-Surgical MRI Guided US", Proceedings of SPIE, vol. 9786, 2016.
Chen H. et al., "Ultrasound Standard Plane Detection Using a Composite Neural Network Framework", IEEE Transactions on Cybernetics, vol. 47, No. 6, pp. 1576-1586, Jun. 2017.
Wein W. et al., "Automatic CT-Ultrasound Registration for Diagnostic Imaging and Image-Guided Intervention", Medical Image Analysis, 12, 2008, pp. 577-585.

* cited by examiner

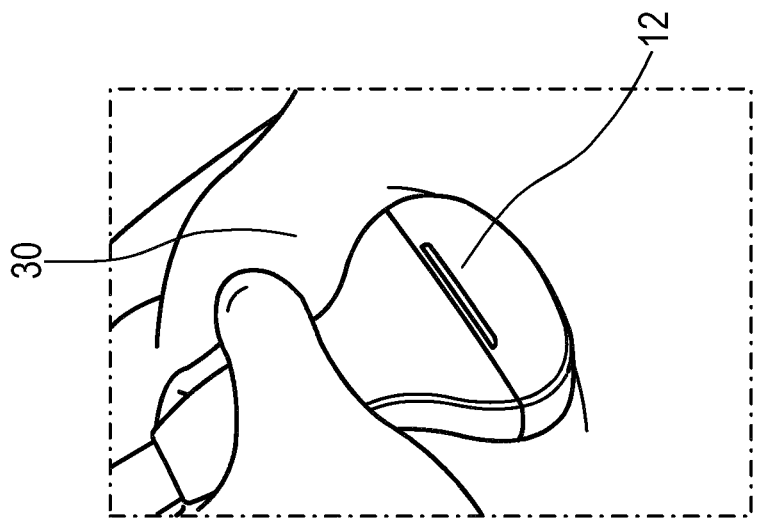
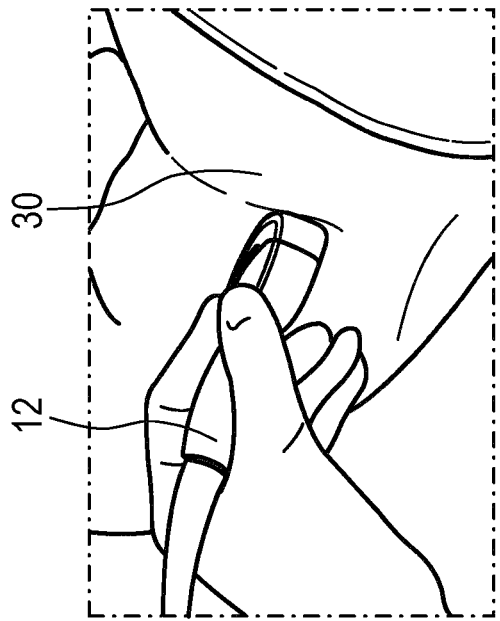
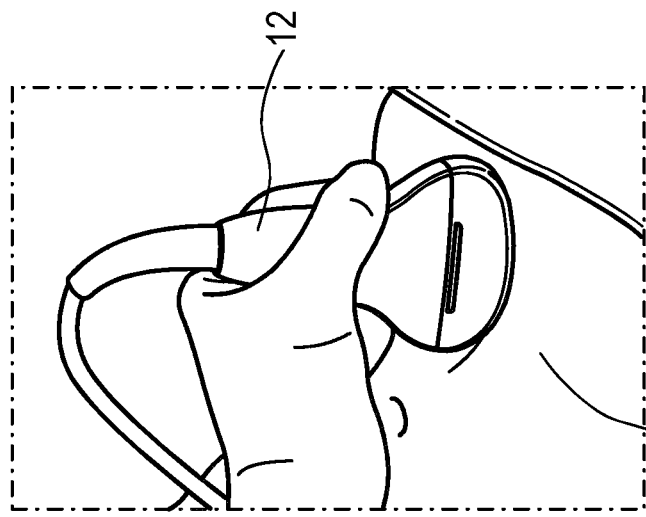

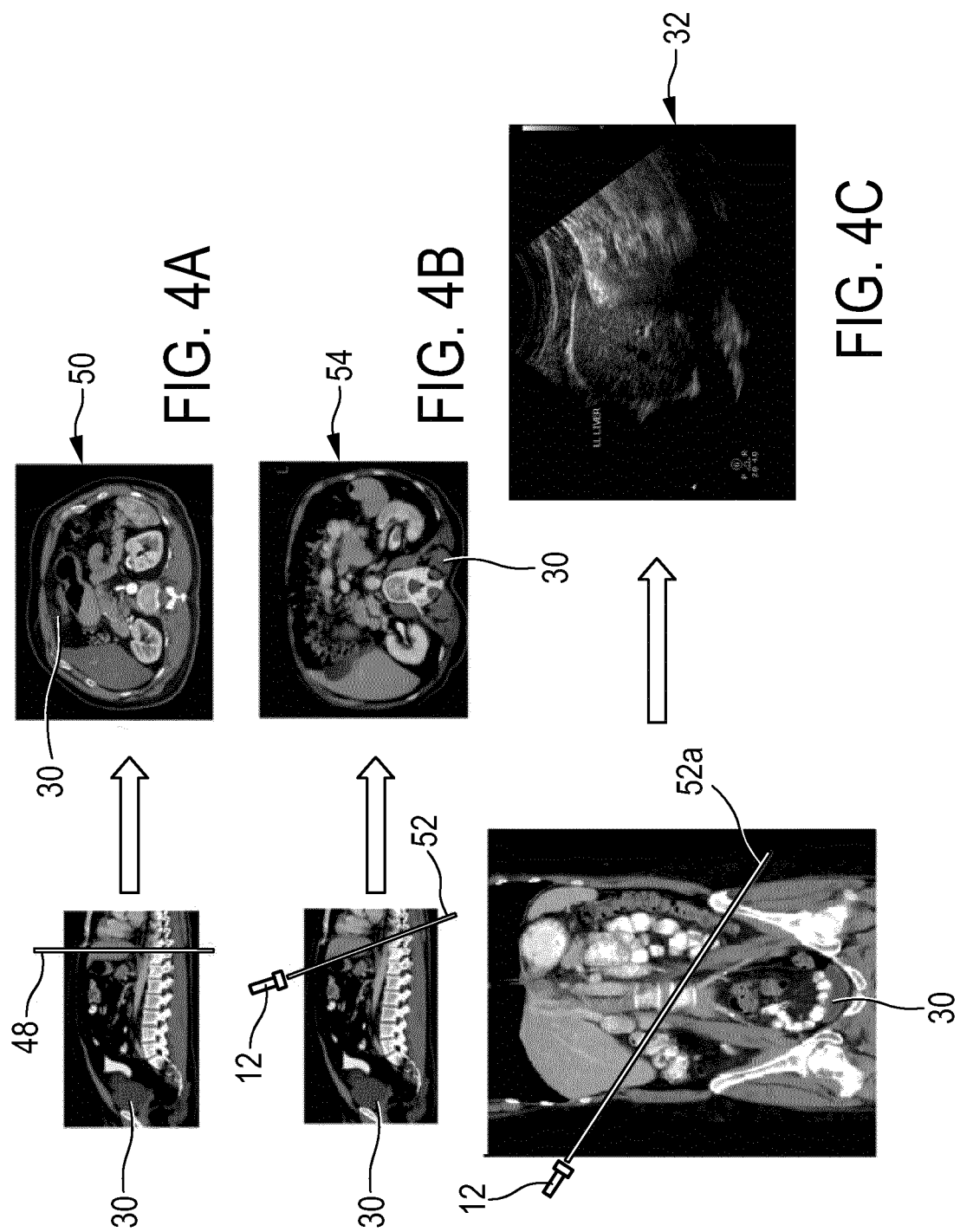

US 12,106,496 B2

LOWER TO HIGHER RESOLUTION IMAGE FUSION

CROSS-REFERENCE TO RELATED APPLICATIONS

This patent application claims the priority benefit under 35 U.S.C. § 371 of International Patent Application no. PCT/EP2019/061154, filed May 1, 2019, which claims the benefit of European Patent Application No. EP18170235.8, filed on May 1, 2019. These applications are hereby incorporated by reference herein in their entirety.

FIELD OF THE INVENTION

The present invention relates to a medical imaging device for generating fusion images, a medical imaging system for generating fusion images, a method for operating the medical imaging device, and a computer program. In particular the present invention relates to a medical imaging device for generating fusion images based on higher resolution reference images of an object and lower resolution images of the object.

BACKGROUND OF THE INVENTION

WO 2009/053896 A2 shows a localizer and registration unit that compares a 3D ultrasound image from a memory with a 3D diagnostic image from a memory which determines a baseline transform which registers the 3D diagnostic and ultrasound volume images. The target region continues to be examined by an ultrasound scanner which generates a series of real-time 2D or 3D ultrasound or other lower resolution images. The localizer and registration unit compares one or a group of the 2D ultrasound images with the 3D ultrasound image to determine a motion correction transform. An image adjustment processor or program operates on the 3D diagnostic volume image with the baseline transform and the motion correction transform to generate a motion corrected image that is displayed on an appropriate display.

US 2017/0132796 A1 shows a medical viewing system with a viewing plane determination. The medical viewing system comprises an X-ray image acquisition device, an echocardiographic image acquisition device, and a processing unit. The X-ray image acquisition device is adapted to acquire an X-ray image in an X-ray imaging plane. The echocardiographic image acquisition device is adapted to acquire a plurality of echocardiographic images. The processing unit is adapted for a determination of an indicator in the X-ray image indicating a viewing plane for an echocardiographic image. The processing unit is further adapted for registering or fusing the X-ray image and the plurality of echocardiographic images together, and for then providing an echocardiographic image in the identified viewing plane.

The article "Single slice US-MRI registration for neurosurgical MRI guided US" of U. Pardasani et al., Proc. SPIE 9786, 2016 shows a method for image-based ultrasound (US) to magnetic resonance imaging (MRI) registration. Magnetic resonance (MR) images are acquired pre-operatively. A tracked US session is performed for acquiring US images. The MR data is skull stripped and a segmented dural surface is estimated. US slices that have expert identified landmarks in them are searched for from a reconstructed US volume within 0.3 mm. For each of the US slices with a landmark a rectangular craniotomy site is created by projecting a head of a US probe onto the dural surface. The best US probe pose is searched using a metric and optimization approach. An error between the expert identified landmarks in the US probe slice and the MRI volume is calculated.

SUMMARY OF THE INVENTION

It can be seen as an object of the present invention to provide a medical imaging device for generating fusion images, a medical imaging system for generating fusion images, a method for operating the medical imaging device, a computer program, and a computer readable medium which allow to improve the generation of fusion images.

In a first aspect of the present invention a medical imaging device for generating fusion images of an object is presented. The medical imaging device comprises a lower resolution image scanning unit, a memory, and an image processing unit. The lower resolution image scanning unit is configured for acquiring lower resolution images of the object with specific image scanning geometries. The memory is configured for storing higher resolution reference images of the object. The image processing unit is configured for generating fusion images of the object. The image processing unit comprises an image scanning geometry determination unit, an oblique higher resolution image generation unit, an image registration unit, a feature information extraction unit, and an image fusion unit. The image scanning geometry determination unit is configured to determine the specific image scanning geometry used for acquiring a respective lower resolution image based on a machine learning algorithm that uses at least one feature in at least one region of interest in the respective lower resolution image as input. The oblique higher resolution image generation unit is configured to generate image scanning geometry matching oblique higher resolution images based on the higher resolution reference images and the determined specific image scanning geometries used for acquiring the respective lower resolution images. The image registration unit is configured to generate registered higher resolution images by registering the oblique higher resolution images with the lower resolution images. The feature information extraction unit is configured to extract current feature information from the lower resolution images. The image fusion unit is configured to map the current feature information on corresponding feature information in the registered higher resolution images in order to generate fusion images.

The lower resolution images and the higher resolution reference images can be medical images. The object can for example be a part of the body of a patient. The medical images can for example be used for cancer management. For cancer management the higher resolution reference images can for example be acquired before the treatment and the lower resolution images can be acquired after the treatment. The treatment can for example be surgery, chemotherapy or radiotherapy. The fusion images can be used to study the progression of the cancer. The fusion images have a higher resolution than the lower resolution images and comprise the current feature information of the lower resolution images, i.e. the feature information acquired after the treatment. The current feature information can for example be a tumour contour. This allows to study the progression of cancer with fusion images that have an improved resolution and cause less radiation exposure during acquisition than by directly using higher resolution images, such as computed tomography (CT) images after the treatment.

Acquiring lower resolution images is less expensive and less time consuming. Since the specific image scanning geometry used for acquiring a respective lower resolution image is encoded in the respective lower resolution image, there is no need for an external tracking system. This allows to reduce effects on the medical imaging device from external disturbing fields. Additionally no wired sensors which affect degrees of freedom of the lower resolution image scanning unit during the procedure are required. In contrast to devices that use external tracking systems to determine the image scanning geometry, no clean line of sight is required between the external tracking system and the tracked object.

The image scanning geometry can include probe geometry and patient geometry, e.g., probe position, patient position, and/or probe angle relative to the patient. The medical imaging device allows to account for the probe position relative to the patient position. This allows an increased freedom for positioning the object relative to the medical imaging device.

The medical imaging device can be used to perform real-time image fusion of lower resolution images, such as US images, and higher resolution reference images, such as CT reference images or MR reference images without the need of external tracking devices.

The specific image scanning geometry can be acquired from the lower resolution image. For lower resolution images acquired using a US system, factors affecting the accuracy of the measurement, such as pressure applied on the body for imaging, the amount of gel used, the patient breathing, et cetera are inherently accounted for by the medical imaging device. The medical imaging device allows to determine the specific image scanning geometry with higher accuracy. The degrees of freedom of the medical imaging device and its mobility are preserved. The medical imaging device allows to continuously improve the accuracy of determination while it uses the lower resolution images. The lower resolution images contain information about the object, e.g the part of the body of the patient.

The image scanning geometry determination unit allows to determine the specific image scanning geometry without requiring external fiducials or anatomic landmarks. This allows users with less experience of the anatomy of the object to use the medical imaging device for generating fusion images.

Fusion images acquired in a previous procedure can be provided as higher resolution reference images. This allows to keep the higher resolution reference images updated without requiring to acquire higher resolution images using cost intensive equipment, such as CT systems or MRI systems.

The image registration unit can be configured for registering the oblique higher resolution images with the lower resolution images using a feature-based algorithm. The feature-based algorithm can for example be a segmentation-based registration algorithm, such as deformable image registration method.

The image scanning geometry determination unit can be configured to identify at least one region of interest in the respective lower resolution image by using an automatic segmentation algorithm that segments the respective lower resolution image in regions of interest with features that allow to determine the specific image scanning geometry used for acquiring the respective lower resolution image. The image scanning geometry determination unit can be configured to determine the specific image scanning geometry used for acquiring the lower resolution images using the machine learning algorithm on the regions of interest. The image scanning geometry determination unit can be configured to iteratively increase the number of regions of interest identified by the image scanning determination unit. The image scanning geometry determination unit can for example in a first iterative step identify only one gross region of interest or a specific number of gross regions of interest that include features that allow correctly determining the image scanning geometry with highest probability. The gross regions of interest that include features that allow correctly determining the image scanning geometry with highest probability can for example be one of or a combination of liver, bladder, and/or rectum. These gross regions of interest comprise features that allow to determine the image scanning geometry with more than 90% accuracy. Segmenting only these gross regions of interest and using these gross regions of interest as input to the machine learning algorithm allows an efficient determination of the image scanning geometry in short time and with less computational resources. This eventually allows an improved image registration and image fusion, i.e., registering the oblique higher resolution images with the lower resolution images and generating fusion images. The image scanning geometry determination unit can iteratively increase the number of regions of interest identified by the automatic segmentation algorithm. The image scanning geometry determination unit can iteratively increase the number of regions of interest provided to the machine learning algorithm in the further iterative steps such that the accuracy of the determination of the image scanning geometry can be further increased.

The machine learning algorithm can be trained to determine the specific image scanning geometry based on the features in the regions of interest. The machine learning algorithm can be trained using deep learning methods. Deep learning allows the machine learning algorithm to independently learn features and patterns provided in the input data to the machine learning algorithm. The machine learning algorithm can be trained using a supervised training method, semi-supervised method, or an unsupervised training method based on a library of regions of interests of lower resolution images with known specific image scanning geometry and/or lower resolution images with known specific image scanning geometry. During the training phase, the machine learning algorithm can learn which features from which regions of interest have the highest probability for correctly determining the image scanning geometry. This allows to identify gross regions of interest with features that have the highest probability for correctly determining the image scanning geometry. The identification of the gross regions of interest with features that have the highest probability for correctly determining the image scanning geometry allows to determine an order of regions of interest to be used in the iterative steps for identifying regions of interest in the iterative process that can be performed using the automatic segmentation algorithm. The image scanning determination unit can be configured to add features in the iterative steps for identifying regions of interest in an order that depends on the probability of the feature for correctly determining the image scanning geometry as determined during the training phase of the machine learning algorithm.

The machine learning algorithm can for example be trained for determining probe angles of the lower resolution image scanning unit relative to the object from the features in the regions of interest. The machine learning algorithm can be trained using a supervised training method or an unsupervised training method based on a library of regions of interests of lower resolution images with known probe angles of the lower resolution image scanning unit and/or lower resolution images with known probe angles of the lower resolution image scanning unit. If the object is for example a body of a patient or a part of the body of the patient, the regions of interest can be structures such as organs, tissues, cavities, and/or veins of the patient. One region of interest can for example be the urinary bladder. The urinary bladder contour allows to determine whether the lower resolution image was acquired from anterior-posterior or posterior-anterior. Another region of interest can for example be the liver. The liver contour allows to determine the probe direction in left-right axis. By considering more regions of interest, such as organs and tissues of the patient, the accuracy of the specific image scanning geometry or in particular the probe angle can be increased.

The machine learning algorithm can be trained by a method for training the machine learning algorithm comprising the steps:

providing lower resolution images of a three-dimensional training object with known specific image scanning geometries, providing higher resolution reference images of the three-dimensional training object with the same specific image scanning geometries as the lower resolution images of the three-dimensional training object, segmenting the lower resolution images of the three-dimensional training object and the higher resolution reference images of the three-dimensional training object in order to identify regions of interest with features that allow to determine the specific image scanning geometry of the respective image, registering the lower resolution images of the three-dimensional training object with the higher resolution images of the three-dimensional training object in order to generate registered images of the three-dimensional training object, slicing the registered images of the three-dimensional training object into oblique slices of the three-dimensional training object with known image slicing geometries in order to derive oblique registered images, and providing the oblique registered images and the known image slicing geometries to the machine learning algorithm in order to train the machine learning algorithm for determining the specific image scanning geometry used for acquiring a respective lower resolution image of an unknown object based on the machine learning algorithm that uses at least one feature in at least one region of interest in the respective lower resolution image of the unknown object as input. The image scanning geometries of the lower resolution images of the unknown object can be related to the image slicing geometries of the oblique registered images.

The registered images can be sliced into random slices, i.e., the slicing can be performed such that randomly sliced oblique registered images are generated. The slicing can alternatively be performed based on predetermined image slicing geometries. The step of training the machine learning algorithm allows the machine learning algorithm to relate features, e.g. geometric features, of different regions of interest to the image slicing geometry, e.g. an image slicing angle. This allows the machine learning algorithm to be used to determine the image scanning geometries used for acquiring lower resolution images based on an effective training.

The image scanning geometry determination unit can be configured to iteratively increase the number of features used for determining the specific image scanning geometry used for acquiring the respective lower resolution image in each iterative step until a value of a cost function of the machine learning algorithm is below a specific threshold value. Iteratively increasing the number of features used for determining the specific image scanning geometry can relate to the iterative process of identifying regions of interest and to providing the features to the machine learning algorithm as input. This allows the image processing unit to iteratively minimize the cost function of the machine learning algorithm and to improve the accuracy of the determination of the specific image scanning geometry. An improved determination of the specific image scanning geometry allows to improve the quality of the oblique high resolution images and therefore of the registered higher resolution images and eventually of the fusion images. Furthermore iteratively increasing the number of features used for determining the specific image scanning geometry used for acquiring the respective lower resolution image lowers the processing time and thus reduces the delay in the real-time image fusion processing that can be performed by the medical imaging device. In particular using only a limited number of features allows a faster processing as not all features have to be processed by the machine learning algorithm for determining the specific image scanning geometry. The order of the features to be added in the iterative steps can be related to the probability of the feature for correctly determining the image scanning geometry as determined during the training phase of the machine learning algorithm. The image scanning determination unit can be configured to add features in the iterative steps in an order that depends on the probability of the feature for correctly determining the image scanning geometry as determined during the training phase of the machine learning algorithm.

The cost function of the machine learning algorithm can for example be a cost function used for registration techniques, such as the same cost function as used for the registration of the oblique higher resolution images with the lower resolution images. The lower resolution image scanning unit can be an US image scanning unit for acquiring US images. US image scanning units allow to reduce exposure to radiation and reduce cost. The lower resolution images can be US images. The lower resolution images can be acquired using an US imaging system.

The higher resolution reference images can be CT images or MR images. The higher resolution reference images can be acquired using a CT system or a MRI system. The higher resolution reference images can be stored in the memory. Alternatively or additionally higher resolution reference images can be acquired by connecting the medical imaging device to a higher resolution imaging scanning unit and acquiring higher resolution reference images of the object. Using CT images and MRI images as high resolution reference images allows generation of fusion images with a high resolution.

The current feature information can be tumour information. The current feature information can for example be a tumor contour. Using tumour contour as current feature information allows to study the progression of cancer of a patient and in particular to study the effect of the treatment.

The image processing unit can comprise a three-dimensional modelling unit. The three-dimensional modelling unit can be configured to generate a three-dimensional model from the fusion images. The oblique higher resolution images can be registered with the lower resolution images in different planes. The three-dimensional modelling unit can be configured to generate the three-dimensional model under the condition that a specific number of fusion images in different planes has been generated and/or is available. The three-dimensional model can for example be generated from a series of fusion images. The series of fusion images can for example be provided in form of oblique two-dimensional slices of a three-dimensional model of the object. The three-dimensional modelling unit can be configured to generate a three-dimensional model of the object from the fusion images when a threshold number of fusion images in different planes has been generated and/or is available. The three-dimensional model allows an improved view of the object.

The object can be a part of a body and the regions of interest can be structures in the part of the body, such as organs, cavities, veins, tissues and other regions of interest. Features of the regions of interest can for example be their contours, edges, area sizes, volumes, or other features. The contours of the regions of interest, in particular of the structures in the part of the body allow to derive the specific image scanning geometry. The machine learning algorithm can be trained based on a library including structures in the part of the body in order to determine the specific image scanning geometry. This allows to encode the specific image scanning geometry in the lower resolution images and to derive the specific image scanning geometry from the lower resolution images without the need of external tracking systems.

The medical imaging device can be configured to perform real-time image fusion for image guided medical procedures, such as for biopsy, surgery, angiography, et cetera. In particular the medical imaging device can for example be configured for lesional identification and/or image guided percutaneous needle biopsy or ablation of an indeterminate or malignant lesion.

The medical imaging device can be used in adaptive radiotherapy. Adaptive radiotherapy is typically performed for a predetermined number of days. The adaptive radiotherapy can for example be performed over 25 to 30 days. In adaptive radiotherapy, a treatment plan is often adapted due to changing anatomy of a patient, such as changing tumour volume. Adapting the plan typically involves acquiring higher resolution images, such as CT images or cone beam CT (CBCT) images, re-contouring of the tumour volume and organs, i.e., segmenting the CT images, and planning quality assessment, and optimizing beam parameters for the radiotherapy for the changed tumour volume. If the radiotherapy is not performed adaptively, the beam applied to the patient potentially misses tumour volume and/or an excessive dose of radiation is applied to healthy tissue surrounding the tumour volume. Information provided by fusion images can be used for deciding whether adaptive radiotherapy needs to be performed, i.e., whether the treatment plan needs to be adapted. In particular fusion images, e.g. based on US images and CT reference images, can be used to determine whether drastic changes occurred in the anatomy of the patient over time. If any drastic changes are detected, the treatment plan can be adapted. Otherwise the treatment can be continued without requiring to adapt the treatment plan. This allows to reduce the amount of radiation exposure and time spent in acquiring another CT image. In particular in the prior art acquiring CT images of the patient and registering them with previous CT images in order to determine whether adaption of the treatment plan is required, can take between 30 to 45 minutes. The medical imaging device allows to acquire lower resolution images, such as US images, when the patient is positioned for receiving radiotherapy treatment. Fusion images can be generated in real-time based on the US images in order to determine whether a change of anatomy of the patient occurred. When no change occurred, the treatment can be performed. Otherwise the treatment plan can be adapted. This allows a faster processing and reduced exposure to X-ray radiation.

In a further aspect of the present invention a medical imaging system is presented. The system comprises a medical imaging device according to one of the claims 1 to 7 or any embodiment of the medical imaging device and a higher resolution image scanning unit. The higher resolution image scanning unit is configured for acquiring higher resolution reference images with specific image scanning geometries.

The higher resolution image scanning unit can comprise a CT unit and/or a MRI unit, i.e., a CT unit, a MRI unit, or a CT unit and a MRI unit. The CT unit can be configured for acquiring CT images. The MRI unit can be configured for acquiring MR images.

In a further aspect of the present invention a method for operating the medical imaging device according to one of the claims 1 to 7 or any embodiment of the medical imaging device is presented. The method comprises the steps:
providing higher resolution reference images of an object,
providing lower resolution images of the object with specific image scanning geometries,
determining the specific image scanning geometries used for acquiring respective lower resolution images based on the machine learning algorithm that uses at least one feature in at least one region of interest in the respective lower resolution images as input,
generating image scanning geometry matching oblique higher resolution images based on the higher resolution reference images and the determined specific image scanning geometries used for acquiring the respective lower resolution images,
registering the oblique higher resolution images with the lower resolution images in order to generate registered higher resolution images,
extracting current feature information from the lower resolution images, and
mapping the current feature information on corresponding feature information in the registered higher resolution images in order to generate fusion images.

The fusion images have a higher resolution than the lower resolution images and comprise the information of the lower resolution images. The method can comprise the step:
identifying at least one region of interest in the respective lower resolution image by using an automatic segmentation algorithm that segments the respective lower resolution image in regions of interest with features that allow to determine the specific image scanning geometry used for acquiring the respective lower resolution image.

Alternatively or additionally the method can comprise the step:
determining the specific image scanning geometry used for acquiring the respective lower resolution image using the machine learning algorithm on at least one of the regions of interest. The machine learning algorithm can be a machine learning algorithm that was trained to determine the specific image scanning geometry based on the features in the regions of interest.

The method can comprise a step of training the machine learning algorithm. The step of training can comprise a step of training the machine learning algorithm based on a library of regions of interest of the lower resolution images with known specific image scanning geometries, e.g. known probe angles. The machine learning algorithm can be trained using a supervised training method or an unsupervised training method.

The step of training the machine learning algorithm can alternatively or additionally comprise the steps:
- providing lower resolution images of a three-dimensional training object with known specific image scanning geometries,
- providing higher resolution reference images of the three-dimensional training object with the same specific image scanning geometries as the lower resolution images of the three-dimensional training object,
- segmenting the lower resolution images of the three-dimensional training object and the higher resolution reference images of the three-dimensional training object in order to identify regions of interest with features that allow to determine the specific image scanning geometry of the respective image,
- registering the lower resolution images of the three-dimensional training object with the higher resolution images of the three-dimensional training object in order to generate registered images of the three-dimensional training object,
- slicing the registered images of the three-dimensional training object into oblique two-dimensional slices of the three-dimensional training object with known image slicing geometries in order to derive oblique registered images, and
- providing the oblique registered images and the known image slicing geometries to the machine learning algorithm in order to train the machine learning algorithm for determining a specific image scanning geometry used for acquiring a respective lower resolution image of an unknown object based on the machine learning algorithm that uses at least one feature in at least one region of interest in the respective lower resolution image of the unknown object as input. The image scanning geometries of the lower resolution images of the unknown object are related to the image slicing geometries of the oblique registered images.

The lower resolution images of the three-dimensional training object and the higher resolution images of the three-dimensional training object comprise information of the three-dimensional object, i.e., a three-dimensional model of the training object can be generated based on the lower resolution images of the three-dimensional training object and the higher resolution images of the three-dimensional training object. The registered images of the three-dimensional training object can be sliced based on different image slicing geometries that are related to image scanning geometries.

The registered images can be sliced into random slices, i.e., the slicing can be performed such that randomly sliced oblique registered images are generated. The slicing can alternatively be performed based on predetermined image slicing geometries, for example image slicing geometries that correspond to preferred or common image scanning geometries. The step of training the machine learning algorithm allows the machine learning algorithm to relate features, e.g. geometric features, of different regions of interest to the image slicing geometry, e.g. an image slicing angle. The image slicing geometry can be related to the image scanning geometries used for acquiring lower resolution images. This allows the machine learning algorithm to be used to determine the image scanning geometries used for acquiring lower resolution images based on an effective training. The machine learning algorithm trained in the step of training can be used to determine the image scanning geometries used for acquiring lower resolution images.

A cost function of the machine learning algorithm can be iteratively minimized by increasing the number of features used to determine the specific image scanning geometry in each iteration step until a value of the cost function is below a specific threshold value.

The method can comprise the steps:
- increasing the number of features used to determine the specific image scanning geometry, and
- calculate the cost function of the machine learning algorithm. These steps can be repeated together with the step of determining the specific image scanning geometry until the value of the cost function is below a specific threshold value in order to iteratively minimize the cost function of the machine learning algorithm. This allows to improve the accuracy of the specific image scanning geometry. Since only a limited number of features and not all features are processed by the machine learning algorithm in order to determine the specific image geometry, the processing time and resources for processing can be reduced.

The method can comprise a step of selecting a registration set of the oblique higher resolution images for registration based on one or more features of the oblique higher resolution images.

The registering of the oblique higher resolution images with the lower resolution images can be performed using a feature-based algorithm, for example a segmentation-based registration algorithm, such as deformable image registration method.

The lower resolution images can be encoded with the specific image scanning geometry used for acquiring the respective lower resolution image.

In a further aspect of the present invention a method for generating fusion images is presented. The method comprises the steps:
- providing higher resolution reference images of an object,
- providing lower resolution images of the object with specific image scanning geometries,
- determining the specific image scanning geometries used for acquiring respective lower resolution images based on a machine learning algorithm that uses at least one feature in at least one region of interest in the respective lower resolution images as input,
- generating image scanning geometry matching oblique higher resolution images based on the higher resolution reference images and the determined specific image scanning geometries of the respective lower resolution images,
- registering the oblique higher resolution images with the lower resolution images in order to generate registered higher resolution images,
- extracting current feature information from the lower resolution images,
- mapping the current feature information on corresponding feature information in the registered higher resolution images in order to generate fusion images.

In a further aspect of the present invention a computer program for operating the medical imaging device according to claims 1 to 7 or any embodiment of the medical imaging device is presented. The computer program comprises program code means for causing a processor to carry out the method as defined in one of the claims 10 to 13, or any embodiment of the method, when the computer program is run on the processor.

In a further aspect a computer readable medium having stored the computer program of claim 14 is presented. Alternatively or additionally the computer readable medium can have the computer program according to any embodiment of the computer program stored.

It shall be understood that the device of claim 1, the system of claim 8, the method of claim 10, the computer program of claim 14, and the computer readable medium of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIG. 2A shows schematically and exemplarily the acquisition of a lower resolution image in a first image scanning geometry;

FIG. 2B shows schematically and exemplarily the acquisition of a lower resolution image in a second image scanning geometry;

FIG. 2C shows schematically and exemplarily the acquisition of a lower resolution image in a third image scanning geometry;

FIG. 4A shows schematically and exemplarily a CT scan of a body from a side perspective and a slice of a straight CT scan through the body;

FIG. 4B shows schematically and exemplarily a CT scan of the body from the side perspective and a slice of an oblique CT scan corresponding to the image scanning geometry of an US system;

FIG. 4C shows schematically and exemplarily a CT scan of the body from a front perspective and an oblique US scan corresponding to the image scanning geometry of the US system;

DETAILED DESCRIPTION OF EMBODIMENTS

Figure 1:
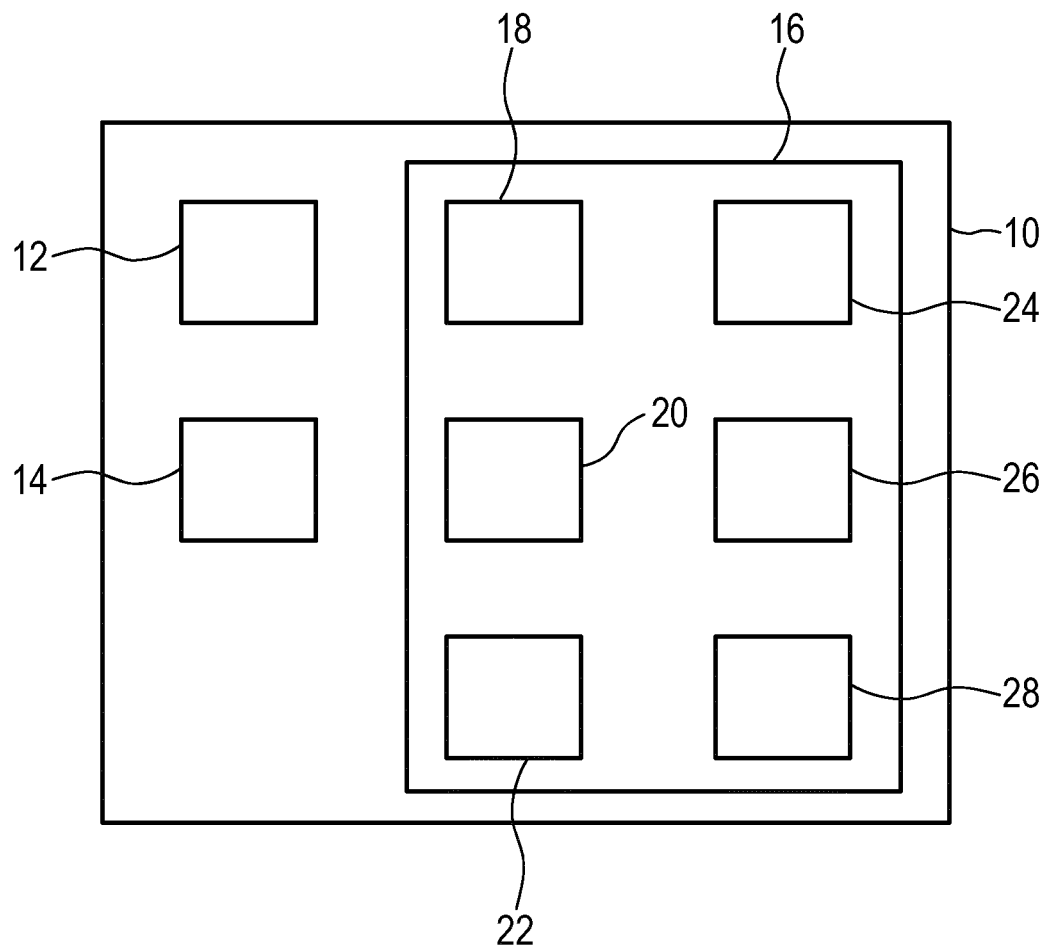
FIG. 1 shows schematically and exemplarily an embodiment of a medical imaging device.

FIG. 1 shows schematically and exemplarily an embodiment of a medical imaging device 10. The medical imaging device 10 can for example be used for follow-up scans of a treatment of a patient. In particular the medical imaging device 10 can be used for generating fusion images of a part of the body of the patient after a major procedure like surgery, chemotherapy or radiotherapy. The fusion images are based on higher resolution reference images, such as CT images or MR images acquired before treatment of the patient and lower resolution images, such as US images acquired after the treatment. In this embodiment CT images of the patient are acquired before the treatment. During the follow-up phase lower resolution images, in this embodiment US images, are acquired and fused with the CT images in order to generate the fusion images.

The medical imaging device 10 comprises a lower resolution image scanning unit in form of an US image scanning unit 12, a computer readable medium in form of memory 14, and a processor in form of an image processing unit 16.

The memory 14 stores higher resolution reference images in form of CT reference images of the body of the patient or a part of the body of the patient. The CT reference images in this embodiment are acquired in different planes such that they correspond to slices of the body of the patient. The CT reference images can be used to generate a three-dimensional model of the part of the body that has been scanned with a CT system in order to acquire the CT reference images. The memory 14 furthermore stores a computer program for operating the medical imaging device 10. The computer program comprises program code means for causing the image processing unit 16 to carry out at least some of the steps of one of the methods presented in FIGS. 6, 7 and 8 when the computer program code is run on the image processing unit 16.

The US image scanning unit 12 is placed on the body 30 of the patient for acquiring US images (see FIGS. 2A, 2B, and 2C). The US images cannot be directly registered with the CT reference images, as the US scanning process involves arbitrary image scanning geometries, in particular US probe geometry and patient geometry.

The image processing unit 16 includes an image scanning geometry determination unit 18, an oblique higher resolution image generation unit 20, an image registration unit 22, a feature information extraction unit 24, an image fusion unit 26, and a three-dimensional modelling unit 28.

The image scanning geometry determination unit 18 determines the specific image scanning geometry used for acquiring a respective US image. The image scanning geometry determination unit 18 executes a machine learning algorithm that uses the contours of organs, tissues, cavities, veins, and other regions of interest of the body of the patient as input and that provides the specific image scanning geometry as output. In other embodiments other features of the regions of interest can be used as input to the machine learning algorithm.

In this embodiment the image scanning geometry determination unit 18 executes an automatic segmentation algorithm for identifying the regions of interest in the US image. The automatic segmentation algorithm segments the US image in regions of interest with features that allow to determine the specific image scanning geometry used for acquiring the US image. The regions of interest include urinary bladder, gallbladder, liver, kidney, diaphragm, and spleen. One feature is the urinary bladder contour which allows to determine whether the US image was acquired from anterior-posterior or posterior-anterior. Another feature is the liver contour which allows to determine the probe direction in left-right axis. By considering more regions of interest of the patient, the accuracy of the specific image scanning geometry and in particular of the probe angle can be increased as more features can be provided as input to the machine learning algorithm.

The image scanning geometry determination unit 18 iteratively increases the number of features used for determining the specific image scanning geometry used for acquiring the respective US image in each iterative step until a value of a cost function of the machine learning algorithm is below a specific threshold value. The specific threshold value in this embodiment is set by the user. Alternatively it can be predetermined. In other embodiments the iterative process can be stopped by an alternative condition, e.g., when the difference of the value of the cost function between two consecutive iteration steps is below a predetermined threshold value.

In this embodiment the image scanning geometry determination unit 18 starts with gross regions of interest, e.g., larger organs, for determining the specific image scanning geometry. In further iteration steps smaller organs and cavities are added and eventually tissues and veins are added as features used by the machine learning algorithm as input. In other embodiments alternative or additional regions of interest, such as small organs, cavities, veins, tissues or other types of regions of interest can be used for determining the specific image scanning geometry.

The machine learning algorithm is trained to determine the specific image scanning geometry based on a library of regions of interest of US images with known specific image scanning geometry. This allows to use the specific image scanning geometry encoded in the regions of interest in the US image for determining the specific image scanning geometry used for acquiring the US image. The machine learning algorithm can also be trained based on the step of training as presented in FIG. 8 or any other method for training the machine learning algorithm.

The oblique higher resolution image generation unit 20 generates image scanning geometry matching oblique higher resolution images in form of oblique CT images that match the specific image scanning geometries of the US images. An oblique CT image is generated by slicing the three-dimensional model of the body formed from the CT reference images according to the specific image scanning geometry (see FIG. 4B). In this embodiment this is performed for all of the US images with determined specific image scanning geometry such that oblique CT images are generated based on the CT reference images and the determined specific image scanning geometries used for acquiring the respective US images. In other embodiments the slicing can also be directly performed on the CT reference images, such that the oblique CT images are generated from the CT reference images and the determined specific image scanning geometries used for acquiring the respective US images.

The image registration unit 22 registers the oblique CT images with the US images using a feature-based algorithm in order to generate registered CT images. In this embodiment the deformable image registration method is used.

The feature information extraction unit 24 extracts current feature information in form of tumour contours from the US images. Alternatively other current feature information, e.g. other tumour information, can be extracted from the US images.

The image fusion unit 26 maps the tumour contour extracted from the US images acquired after the treatment on the tumour contour of the registered CT images that contain the tumour contour acquired before the treatment in order to generate fusion images. The fusion images include the current tumour contour extracted from the lower resolution US images while having the higher resolution of the CT images.

The three-dimensional modelling unit 28 generates a three-dimensional model from the fusion images in order to present a three-dimensional view of the scanned part of the body with the tumour contour after the treatment in higher resolution.

The medical imaging device can be connected to an external device, such as a server or a display (not shown). In other embodiments the medical imaging device can include a display for presenting the three-dimensional model. The medical imaging device can alternatively or additionally store the fusion images and the three-dimensional model in the memory. The fusion images and the three-dimensional model can be provided to the external device via a wired or wireless connection (not shown). The fusion images can also be used as higher resolution reference images in subsequent use of the medical imaging device.

FIGS. 2A, 2B, and 2C show the US image scanning unit 12 in contact with an object in form of a body 30 of a patient in three different image scanning geometries for acquiring US images. As US scans can be performed with arbitrary US probe geometry, the US images acquired with the specific image scanning geometry can generally not be directly registered with other types of images and in particular not with CT images or MR images that are derived as slices of the body of the patient using a CT system or MR system.

FIGS. 3A, 3B, 3C, and 3D show exemplary US images 32, 32a, 32b, and 32c acquired from further image scanning geometries.

Figure 3B:
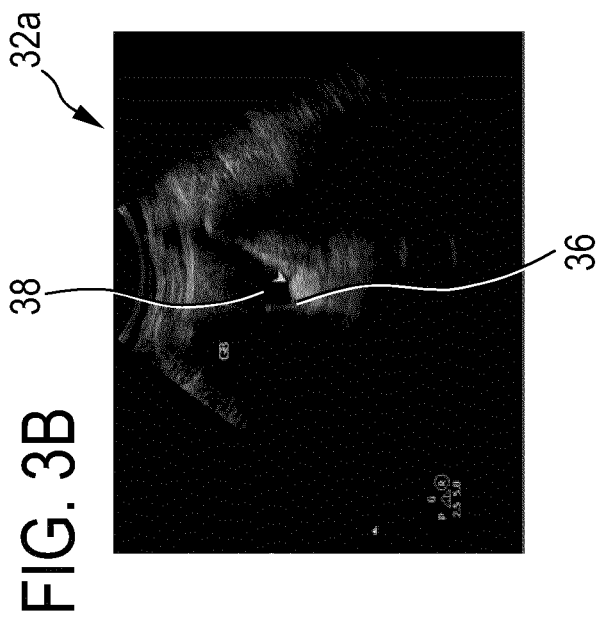
FIG. 3B shows schematically and exemplarily an acquired lower resolution image in a fifth image scanning geometry.
Figure 3D:
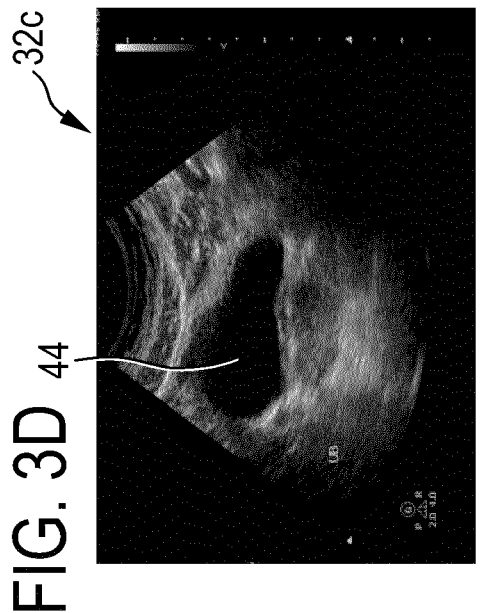
FIG. 3D shows schematically and exemplarily an acquired lower resolution image in a seventh image scanning geometry.
Figure 3A:
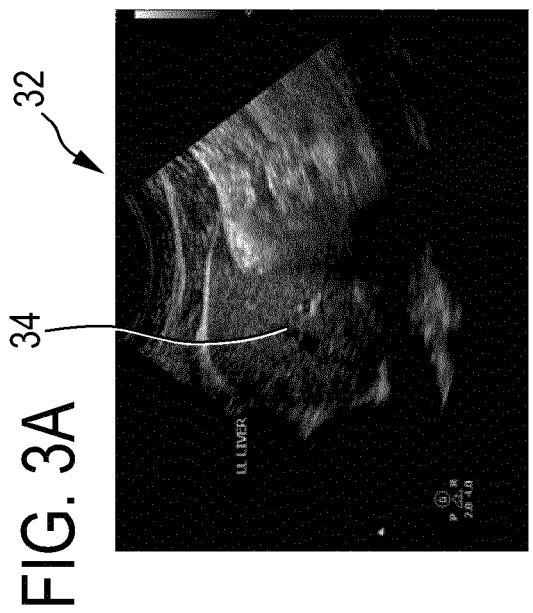
FIG. 3A shows schematically and exemplarily an acquired lower resolution image in a fourth image scanning geometry.
Figure 3C:
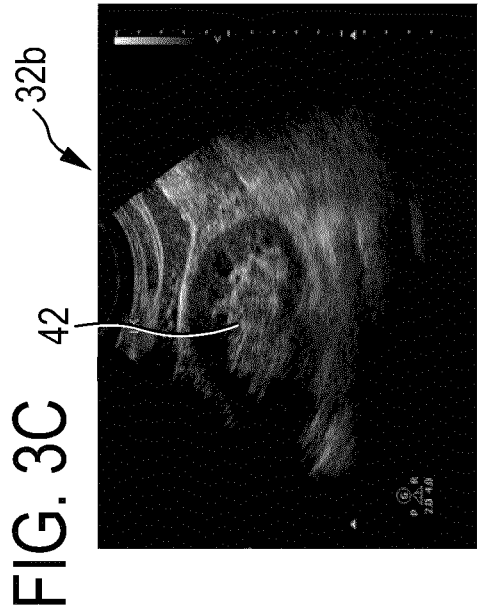
FIG. 3C shows schematically and exemplarily an acquired lower resolution image in a sixth image scanning geometry.

In FIG. 3A the automatic segmentation algorithm identified liver 34, i.e. a gross region of interest, that can be used for determining the specific image scanning geometry used for acquiring the US image 32. In further iterative steps the automatic segmentation algorithm can identify other regions of interest (not shown), In FIG. 3B the automatic segmentation algorithm identified gallbladder neck 36 and gallbladder 38 that can be used for determining the specific image scanning geometry used for acquiring the US image 32a. In further iterative steps the automatic segmentation algorithm can identify other regions of interest (not shown), In FIG. 3C the automatic segmentation algorithm identified left kidney 42 that can be used for determining the specific image scanning geometry used for acquiring the US image 32b. In further iterative steps the automatic segmentation algorithm can identify other regions of interest (not shown), In FIG. 3D the automatic segmentation algorithm identified urinary bladder 44 that can be used for determining the specific image scanning geometry used for acquiring the US image 32c. In further iterative steps the automatic segmentation algorithm can identify other regions of interest (not shown), FIG. 4A shows a CT image of body 30 of a patient in a side perspective and normal axial plane 48 used by CT systems for generating CT image 50. CT image 50 corresponds to a two-dimensional slice of the body 30. A series of CT images can be acquired in order to allow the generation of a three-dimensional model of the body 30 based on the series of the CT images.

FIG. 4B shows a CT image of the body 30 of the patient in the side perspective and an oblique plane 52 that corresponds to the specific image scanning geometry used for acquiring a US image with US image scanning unit 12. The specific image scanning geometry used for acquiring the US image is determined by the image scanning geometry determination unit. An oblique CT image 54 is subsequently generated by the oblique higher resolution image generation unit based on the series of the CT images and the determined specific image scanning geometry. Alternatively the higher resolution image generation unit can use the three-dimensional model of the body 30 generated from the series of CT images as input for generating the oblique CT image.

FIG. 4C shows a CT image of the body 30 of the patient from a front perspective, an oblique plane 52a that corresponds to the specific image scanning geometry used for acquiring an US image with US image scanning unit 12 and the respective US image 32 acquired from the scan.

Figure 5:
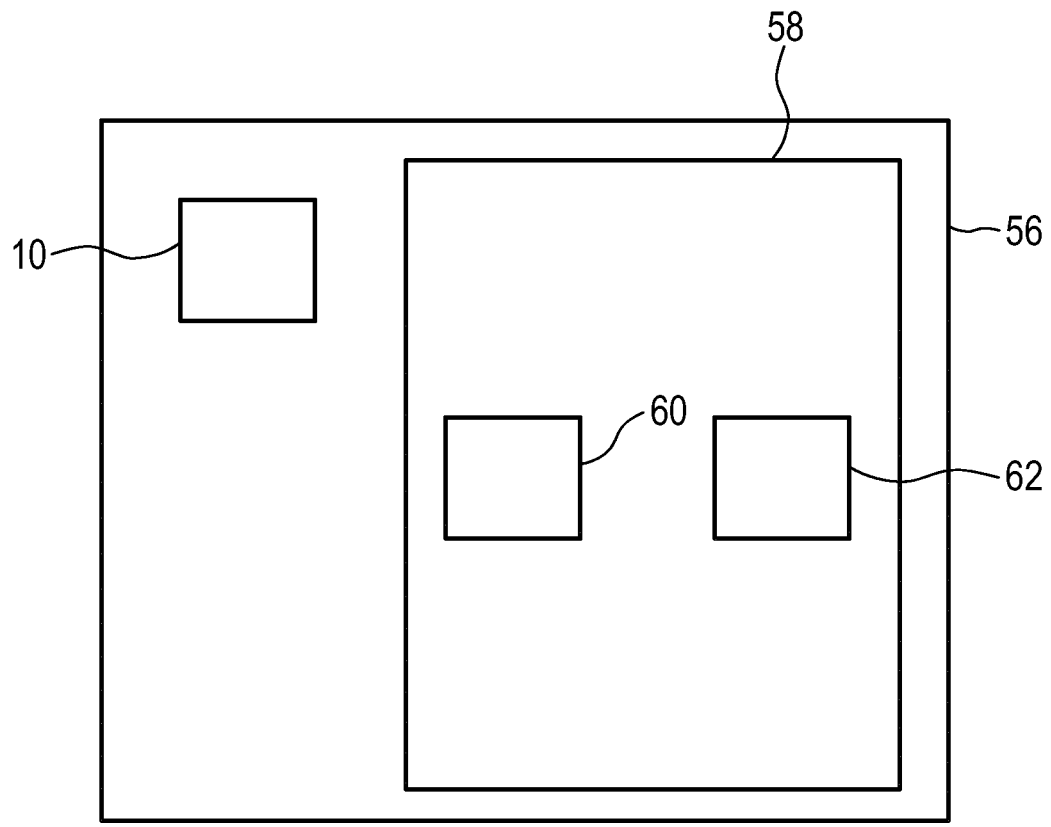
FIG. 5 shows schematically and exemplarily an embodiment of a medical imaging system.

FIG. 5 shows an embodiment of a medical imaging system 56. The medical imaging system 56 includes a medical imaging device 10 as presented in FIG. 1 and a higher resolution image scanning unit 58. The medical imaging system 56 can also include another embodiment of the medical imaging device (not shown).

The higher resolution image scanning unit 58 includes a CT system 60 and a MRI system 62. The CT system 60 can be used for acquiring CT images and the MRI system 62 can be used for acquiring MRI images. The CT images and MRI images can be used as higher resolution reference images in the medical imaging device 10 for generating fusion images based on US images and the CT images or the MRI images.

Figure 6:
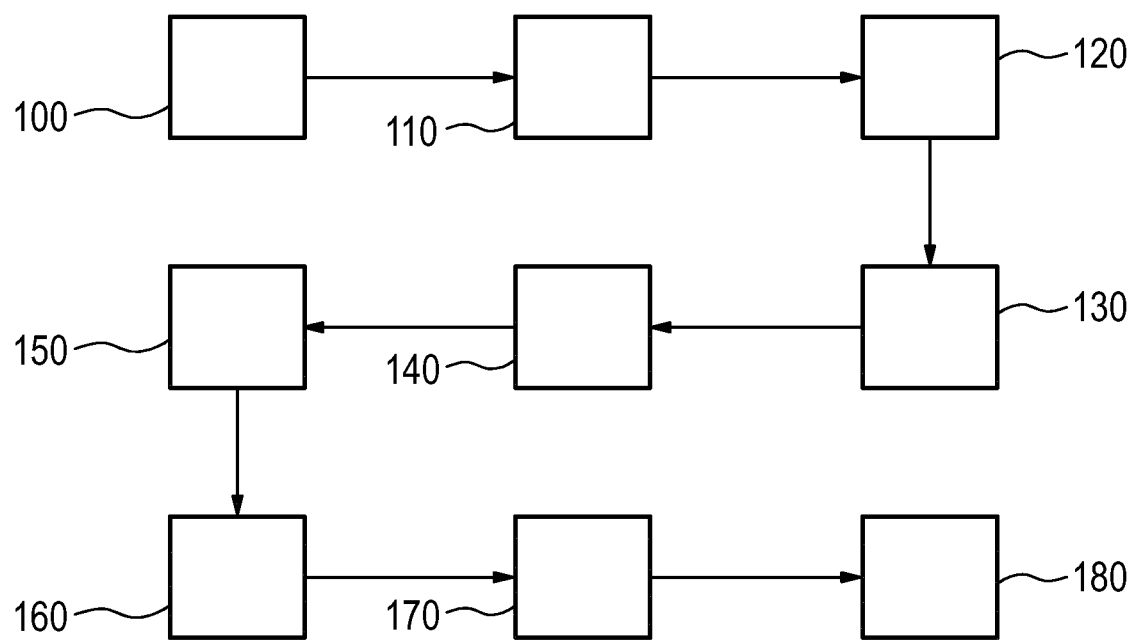
FIG. 6 shows a first embodiment of a method for operating the medical imaging device.

FIG. 6 shows a first embodiment of a method for operating a medical imaging device, e.g. the medical imaging device according to the embodiment presented in FIG. 1.

In step 100 higher resolution reference images in form of CT reference images of an object in form of a body of a patient are provided.

In step 110 lower resolution images in form of US images of the body with specific image scanning geometries are provided.

In step 120 the US images are segmented by an automatic segmentation algorithm which identifies various regions of interest in the US image, such as the urinary bladder, the liver, and other organs and tissues, that can be used for determining the specific image scanning geometries used for acquiring the US images.

In step 130 the specific image scanning geometries used for acquiring respective US images are determined based on a machine learning algorithm. Features of the regions of interest, such as the contour of the urinary bladder or the liver are used by the machine learning algorithm to determine the specific image scanning geometries. The machine learning algorithm has been trained with a library of regions of interest containing features that allow to determine the specific image scanning geometries. The machine learning algorithm is provided with the features of the regions of interest of the respective US images and determines the specific image scanning geometries used for acquiring the respective US images. Alternatively the machine learning algorithm can be trained with a library of lower resolution images with known specific image scanning geometries (not shown). The machine learning algorithm can also be trained by the training step as presented in FIG. 8.

In step 140 image scanning geometry matching oblique higher resolution images in form of oblique CT images are generated based on the CT reference images and the determined specific image scanning geometries used for acquiring the respective US images.

In step 150 the oblique CT images are registered with the US images in order to generate registered CT images.

In step 160 current feature information in form of tumour contours are extracted from the US images.

In step 170 the tumour contours extracted from the US images are mapped on corresponding tumour contours in the registered CT images in order to generate fusion images.

In step 180 a three-dimensional model of the body is generated based on the fusion images. In other embodiments step 180 can be performed only for the case that a predetermined number of fusion images from different planes is available.

The steps 100, 110, and 160 can also be performed in any other order, as long as steps 100 and 110 are performed before the other steps are performed and step 160 is performed before step 170. Steps 120 and 180 are optional.

Figure 7:
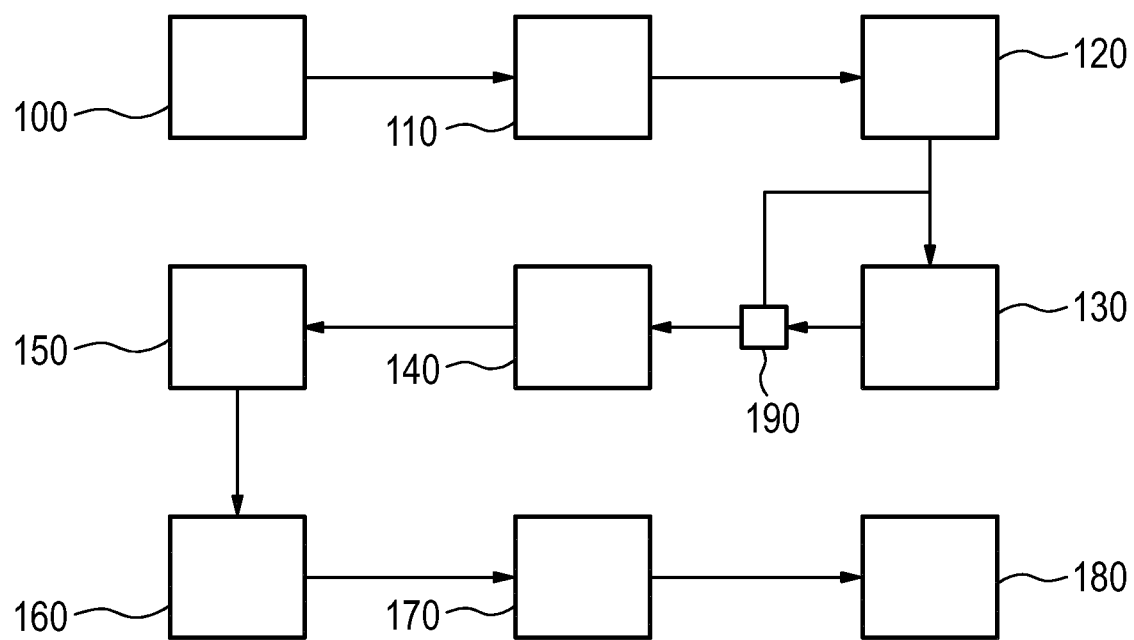
FIG. 7 shows a second embodiment of the method for operating the medical imaging device

FIG. 7 shows a second embodiment of the method. This embodiment includes the additional step 190 between steps 130 and 140.

The second embodiment of the method is similar to the first embodiment of the method and includes essentially the same steps. In contrast to the first embodiment, in the second embodiment a cost function of the machine learning algorithm is iteratively minimized by increasing the number of features used to determine the specific image scanning geometry in each iteration step of an iterative cycle until a value of the cost function is below a specific threshold value.

In step 190 it is determined whether the value of the cost function is below the threshold value. If the value of the cost function is not below the threshold value, step 130 is repeated. If the value of the cost function is below the threshold value, the iterative cycle is ended and step 140 is performed. Step 130 is thus repeated until the value of the cost function is below the specific threshold value. In other embodiments other ending conditions for the iterative cycle can be applied, e.g., a threshold difference value of the cost function between two consecutive iterations or any other stop condition. Adding further features to the input to the machine learning algorithm allows to improve the accuracy of the determination of the specific image scanning geometry and to eventually improve the quality of the fusion images.

Figure 8:
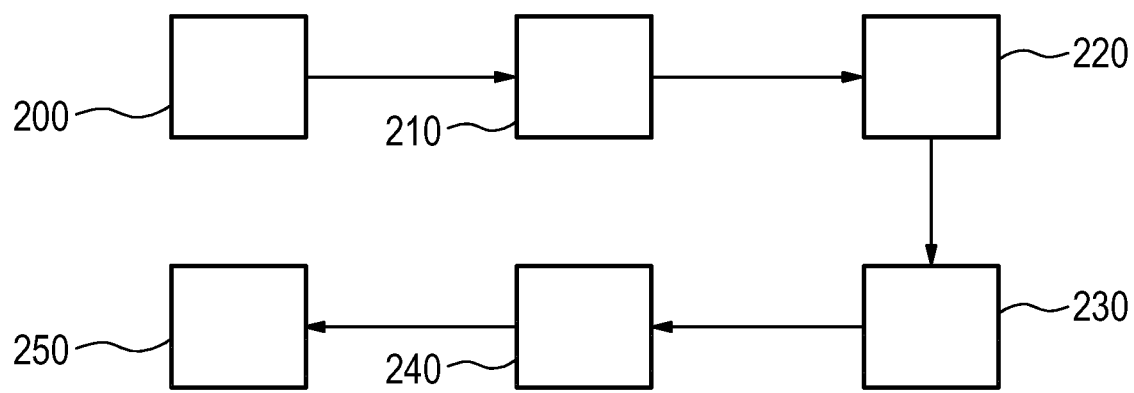
FIG. 8 shows an embodiment of a method for training a machine learning algorithm for determining an image scanning geometry used for acquiring a respective lower resolution image.

FIG. 8 shows an embodiment of a method for training a machine learning algorithm for determining a specific image scanning geometry used for acquiring a respective lower resolution image of an unknown object. The machine learning algorithm can be used to determine the specific image scanning geometries of lower resolution images. In this embodiment the lower resolution images are US images.

In step 200 lower resolution images in form of US images of a three-dimensional training object with known specific image geometries are provided. In this embodiment the training object is a part of a body of a patient, in particular the chest. The machine learning algorithm is therefore trained to determine the specific image scanning geometry used for acquiring a respective US image of the respective part, i.e. the chest, of the body of a patient, i.e., the unknown object is the respective part, i.e., the chest, of the body of a patient in this embodiment. In other embodiments the training object can be a different training object, e.g. another part of a body, such as a head, a leg, an arm, or any other part of the body.

In step 210 higher resolution reference images in form of CT reference images of the three-dimensional training object, i.e. the part of the body of the patient, are provided with the same specific image scanning geometries as the US images of the three-dimensional training object.

In step 220 the US images of the part of the body and the CT reference images of the part of the body are segmented in regions of interest. The regions of interest include features that allow to determine image scanning geometries of the US images. In this embodiment the regions of interest include bladder, liver, kidney, and other organs, tissue, cavities and veins.

In step 230 the US images of the chest are registered with the CT reference images in order to generate registered images of the chest. In this embodiment a feature-based algorithm is used for registering. As the specific image scanning geometries used for acquiring the US images of the training object are known in this embodiment, the US images and the CT images can be registered. The specific image scanning geometries used for acquiring the US images of the training object can for example be obtained by using data acquired using a tracking device that tracks the specific image scanning geometry.

In step 240 the registered images of the part of the body are sliced into oblique two-dimensional slices of the part of the body with known image slicing geometries in order to derive oblique registered images. In this embodiment the slicing is performed randomly. In other embodiments the slicing can be performed based on predetermined image slicing geometries. The predetermined image slicing geometries can for example correspond to preferred or common image scanning geometries, in particular typical probe angles.

In step 250 the oblique registered images and the known image slicing geometries are provided to the machine learning algorithm in order to train the machine learning algorithm for determining the specific image scanning geometry of a respective US image of an unknown object in form of a chest of another patient based on the machine learning algorithm that uses at least one feature in at least one region of interest in the respective US image of the unknown object as input. The image scanning geometries of the US images of the unknown object are related to the image slicing geometries of the oblique registered images.

Steps 200 and 210 can also be performed in opposite order, i.e., first performing step 210 and afterwards performing step 200.

The machine learning algorithm trained according to the method presented in FIG. 8 can be used in the medical imaging device presented in FIG. 1 or any embodiment of the medical imaging device in order to determine the specific image scanning geometries used for acquiring US images. In other embodiments the machine learning algorithm can be trained using other types of lower resolution images and higher resolution reference images. For example instead of training the machine learning algorithm based on US images and CT reference images, US images and MRI reference images can be used.

While the invention has been illustrated and described in detail in the drawings and foregoing description, such illustration and description are to be considered illustrative or exemplary and not restrictive; the invention is not limited to the disclosed embodiments. For example, it is possible to operate the invention in an embodiment wherein the medical imaging device is configured for performing real-time image fusion for image guided medical procedures, such as for biopsy, surgery, angiography, et cetera.

Real-time image fusion performed by the medical imaging device can be used in an embodiment in which the medical imaging device provides fusion images of the liver or the kidney for lesional identification. The information in the fusion images allows to determine whether a lesion in the liver or kidney is likely benign or malignant. This allows to spare an invasive biopsy, where a tissue sample is extracted for pathological examination.

Furthermore the medical imaging device can be used for image guided percutaneous needle biopsy or ablation of an indeterminate or malignant lesion. Typically one or multiple ablation needles are inserted into a center of a lesion or tumour tissue in order to cause coagulative necrosis of tumor tissue by heat application at the needle tip. The fusion images generated by the medical imaging device can be used for determining whether the needle tip is correctly placed. This allows an improved image guidance even for lesions in tissues and organs that move while a patient breathes and/or is in motion. As the needle placement in the center of the lesion or tumour is improved, a risk for complications such as bleeding is reduced.

The medical imaging device can also be used in adaptive radiotherapy. This allows to reduce the amount of radiation exposure and time spent in acquiring another CT image.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit, processor, or device may fulfill the functions of several items recited in the claims. The mere fact that certain measures are recited in mutually different dependent claims does not indicate that a combination of these measures cannot be used to advantage.

Operations like providing higher resolution reference images of an object, providing lower resolution images of the object with specific image scanning geometries, determining the specific image scanning geometries used for acquiring respective lower resolution images based on the machine learning algorithm that uses at least one feature in at least one region of interest in the respective lower resolution images as input, generating image scanning geometry matching oblique higher resolution images based on the higher resolution reference images and the determined specific image scanning geometries used for acquiring the respective lower resolution images, registering the oblique higher resolution images with the lower resolution images in order to generate registered higher resolution images, extracting current feature information from the lower resolution images, mapping the current feature information on corresponding feature information in the registered higher resolution images in order to generate fusion images, identifying at least one region of interest in the respective lower resolution images by using an automatic segmentation algorithm that segments the respective lower resolution images in regions of interest with features that allow to determine the specific image scanning geometries used for acquiring the respective lower resolution images, determining the specific image scanning geometries used for acquiring the lower resolution images using the machine learning algorithm on the regions of interest, et cetera performed by one or several units or devices can be performed by any other number of units or devices. These operations and/or the method can be implemented as program code means of a computer program and/or as dedicated hardware.

A computer program may be stored/distributed on a suitable medium, such as an optical storage medium, or a solid-state medium, supplied together with or as part of other hardware, but may also be distributed in other forms, such as via the Internet, Ethernet, or other wired or wireless telecommunication systems.

Any reference signs in the claims should not be construed as limiting the scope.

The present invention relates to image fusion of lower resolution images and higher resolution reference images of an object. Specific image scanning geometries used for acquiring the lower resolution images are determined based on a machine learning algorithm that uses at least one feature in at least one region of interest in the respective lower resolution images as input. Image scanning geometry matching oblique higher resolution images are generated based on the higher resolution reference images and the determined specific image scanning geometries used for acquiring the respective lower resolution images. The oblique higher resolution images are registered with the lower resolution images in order to generate registered higher resolution images. Current feature information is extracted from the lower resolution images and mapped on corresponding feature information in the registered higher resolution images in order to generate fusion images. This allows generating high resolution fusion images with improved quality.

The invention claimed is:

1. A medical imaging device for generating fusion images of an object comprising:
   a memory storing a computer program;
   a processor coupled to the memory, wherein execution of the computer program by the processor causes the processor to:
   receive acquired lower resolution (LR) images of the object with specific image scanning geometries,
   generate fusion images of the object by:
   identifying at least one region of interest in a respective LR image by using a segmentation algorithm that segments the respective LR image in at least one region of interest having at least one feature that allows the processor to determine a specific image scanning geometry used for acquiring the respective LR image,
   determining, from the respective LR image, the specific image scanning geometry used for acquiring the respective LR image based on a machine learning (ML) algorithm that uses the at least one feature in the at least one region of interest in the respective LR image as input, wherein the at least one feature comprises a contour of the at least one region of interest,
   generating image scanning geometry matching oblique higher resolution (HR) images based on HR reference images and the determined specific image scanning geometries used for acquiring the LR images,
   generating registered HR images by registering the oblique HR images with the LR images,
   extracting current feature information from the LR images, and
   mapping the current feature information on corresponding feature information in the registered HR images.

2. The medical imaging device according to claim 1, wherein execution of the computer program by the processor further causes the processor to iteratively increase a number of features used for determining the specific image scanning geometry used for acquiring the respective LR image in the iterative increases until a value of a cost function of the ML algorithm is below a specific threshold value.

3. The medical imaging device according to claim 1, wherein the ML algorithm is trained by:
   providing LR images of a three-dimensional (3D) training object with known specific image scanning geometries,
   providing HR reference images of the 3D training object with the same specific image scanning geometries as the LR images of the 3D training object,
   segmenting the LR images of the 3D training object and the HR reference images of the 3D training object in regions of interest,
   registering the LR images of the 3D training object with the HR images of the 3D training object to generate registered images of the 3D training object,
   slicing the registered images of the 3D training object into oblique two-dimensional (2D) slices of the 3D training object with known image slicing geometries to derive oblique registered images, and
   providing the oblique registered images and the known image slicing geometries to the ML algorithm to train the ML algorithm for determining the specific image scanning geometry used for acquiring a respective LR image of an unknown object based on the ML algorithm that uses at least one feature in at least one region of interest in the respective LR image of the unknown object as input, wherein the image scanning geometries of the LR images of the unknown object are related to the image slicing geometries of the oblique registered images.

4. The medical imaging device according to claim 1, wherein the LR images are ultrasound images and wherein the HR reference images are computed tomography images or magnetic resonance images.

5. The medical imaging device according to claim 1, wherein execution of the computer program by the processor further causes the processor to generate a 3D model from the fusion images.

6. The medical imaging device according to claim 1, wherein the object is a part of a body and the at least one region of interest is structures in the part of the body.

7. A medical imaging system comprising a medical imaging device according to claim 1, and a HR image scanning unit for acquiring HR reference images with specific image scanning geometries.

8. The medical imaging system comprising a medical imaging device according to claim 1 and a computed tomography system and/or a magnetic resonance imaging system.

9. A method, comprising:
   identifying at least one region of interest in respective LR images by using a segmentation algorithm that segments the respective LR images in at least one region of interest having at least one feature that allows determination of a specific image scanning geometry used for acquiring the respective LR images,
   determining the specific image scanning geometry used for acquiring the respective lower resolution (LR) images based on an ML algorithm that uses the at least one feature in the at least one region of interest in the respective LR images as input, wherein the at least one feature comprises a contour of the at least one region of interest,
   generating image scanning geometry matching oblique higher resolution (HR) images based on HR reference images and the determined specific image scanning geometry used for acquiring the respective LR images,
   registering the oblique HR images with the respective LR images to generate registered HR images,
   extracting current feature information from the respective LR images, and
   mapping the current feature information on corresponding feature information in the registered HR images to generate fusion images.

10. The method according to claim 9,
wherein the ML algorithm is trained to determine the specific image scanning geometry based on the at least one feature in the at least one region of interest.

11. The method according to claim 9, further comprising training the ML algorithm by:
receiving LR images of a 3D training object with known specific image scanning geometries,
receiving HR reference images of the 3D training object with the same specific image scanning geometries as the LR images of the 3D training object,
segmenting the LR images of the 3D training object and the HR reference images of the 3D training object to identify regions of interest with features,
registering the LR images of the 3D training object with the HR images of the 3D training object to generate registered images of the 3D training object,
slicing the registered images of the 3D training object into oblique two-dimensional (2D) slices of the 3D training object with known image slicing geometries to derive oblique registered images, and
providing the oblique registered images and the known image slicing geometries to the ML algorithm to train the ML algorithm for determining the specific image scanning geometry used for acquiring a respective LR image of an unknown object based on the ML algorithm that uses at least one feature in at least one region of interest in the respective LR image of the unknown object as input, wherein the image scanning geometries of the LR images are related to the image slicing geometries of the oblique registered images.

12. The method according to claim 9, wherein a cost function of the ML algorithm is iteratively minimized by increasing a number of features used to determine the specific image scanning geometry in each iteration step until a value of the cost function is below a specific threshold value.

13. A non-transitory computer readable medium having a computer program stored thereon including instructions that when executed by a processor cause the processor to perform the method of claim 9.

14. A medical imaging system comprising a medical imaging device according to claim 1, and an ultrasound imaging system.

15. The method of claim 9, further comprising:
receiving HR reference images of an object,
receiving LR images of the object having specific image scanning geometries.

16. The method of claim 9, wherein the HR images are acquired by a computed tomography system.

17. The method of claim 9, wherein the HR images are acquired by a magnetic resonance imaging system.

18. The method of claim 9, wherein the respective LR images are acquired by an ultrasound imaging system.

* * * * *